US008425486B2

(12) United States Patent
Smisson et al.

(10) Patent No.: US 8,425,486 B2
(45) Date of Patent: Apr. 23, 2013

(54) COLLAPSIBLE FLUID RESERVOIR

(75) Inventors: Hugh F. Smisson, Macon, GA (US);
David C. Field, Snellville, GA (US);
Christopher W. Menard, Macon, GA (US); Brandi L. Bohleber, Macon, GA (US); Hiywot Yilma, Atlanta, GA (US)

(73) Assignee: Smisson-Cartledge Biomedical LLC, Macon, GA (US)

( * ) Notice: Subject to any disclaimer, the term of this patent is extended or adjusted under 35 U.S.C. 154(b) by 577 days.

(21) Appl. No.: 12/624,122

(22) Filed: Nov. 23, 2009

(65) Prior Publication Data

US 2010/0130957 A1 May 27, 2010

Related U.S. Application Data

(60) Provisional application No. 61/116,911, filed on Nov. 21, 2008.

(51) Int. Cl.
*A61B 19/00* (2006.01)
(52) U.S. Cl.
USPC .......................................................... 604/406
(58) Field of Classification Search .................... 604/406
See application file for complete search history.

(56) References Cited

U.S. PATENT DOCUMENTS

| | | | |
|---|---|---|---|
| 1,979,517 A | | 5/1932 | Wohlfeld |
| 3,770,129 A | * | 11/1973 | Brumfield et al. ............. 210/232 |
| 3,892,534 A | | 7/1975 | Leonard |
| 4,026,669 A | | 5/1977 | Leonard et al. |
| 4,047,526 A | * | 9/1977 | Reynolds et al. ............ 604/6.15 |
| 4,424,190 A | * | 1/1984 | Mather et al. .................... 422/46 |
| 4,443,220 A | | 4/1984 | Hauer et al. |
| 4,493,705 A | * | 1/1985 | Gordon et al. ................ 604/122 |
| 4,959,062 A | * | 9/1990 | Gellman ....................... 604/403 |
| 5,019,059 A | * | 5/1991 | Goldberg et al. ............. 604/317 |
| 5,049,146 A | * | 9/1991 | Bringham et al. ........... 604/6.09 |
| 5,192,439 A | | 3/1993 | Roth et al. |
| 5,372,593 A | * | 12/1994 | Boehringer et al. .......... 604/319 |
| 5,720,741 A | * | 2/1998 | Stewart et al. ................ 604/407 |
| 5,800,721 A | | 9/1998 | McBride |
| 5,935,093 A | * | 8/1999 | Elgas et al. .................. 604/6.15 |

(Continued)

OTHER PUBLICATIONS

Lauten, Alexander, et al., The Jena perfusion system: a universal cariopulmonary bypass circuit for cardiac surgery; Interactive CardioVascular and Thoracic Surgery; Oct. 27, 2006. (available at http://icvts.ctsnetjournals.org/cgi/content/full/6/1/1).

(Continued)

*Primary Examiner* — Tatyana Zalukaeva
*Assistant Examiner* — Ginger T Chapman
(74) *Attorney, Agent, or Firm* — Sutherland Asbill & Brennan LLP

(57) ABSTRACT

Described is a collapsible fluid reservoir that may be expanded during use and collapsible to lie substantially flat when not in use. According to one embodiment, a collapsible fluid reservoir can include a substantially non-rigid container having a substantially open proximal end and a substantially sealed distal end opposite the proximal end defining a cavity therein, wherein the distal end includes at least one fluid outlet port extending therethrough. The collapsible fluid reservoir can also include a substantially rigid cap affixed to the proximal end of the non-rigid container and including at least one fluid inlet port extending therethrough and in fluid communication with the cavity.

25 Claims, 8 Drawing Sheets

U.S. PATENT DOCUMENTS

| | | | |
|---|---|---|---|
| 5,941,635 A * | 8/1999 | Stewart | 366/165.5 |
| 6,050,968 A | 4/2000 | Van Driel | |
| 6,337,049 B1 * | 1/2002 | Tamari | 422/44 |
| 6,537,495 B1 * | 3/2003 | Cambron et al. | 422/45 |
| 6,773,426 B2 * | 8/2004 | Tamari | 604/406 |
| 7,131,966 B1 * | 11/2006 | Tamari | 604/406 |
| 7,479,130 B2 * | 1/2009 | Trickett | 604/403 |
| 7,591,812 B1 * | 9/2009 | Tamari | 604/406 |

OTHER PUBLICATIONS

Medtronic, Inc., Cardiotomy Reservoirs/Blood Collection. (available at www.medtronic.com/cardsurgery/arrested_heart/e12_reservoir.html).

* cited by examiner

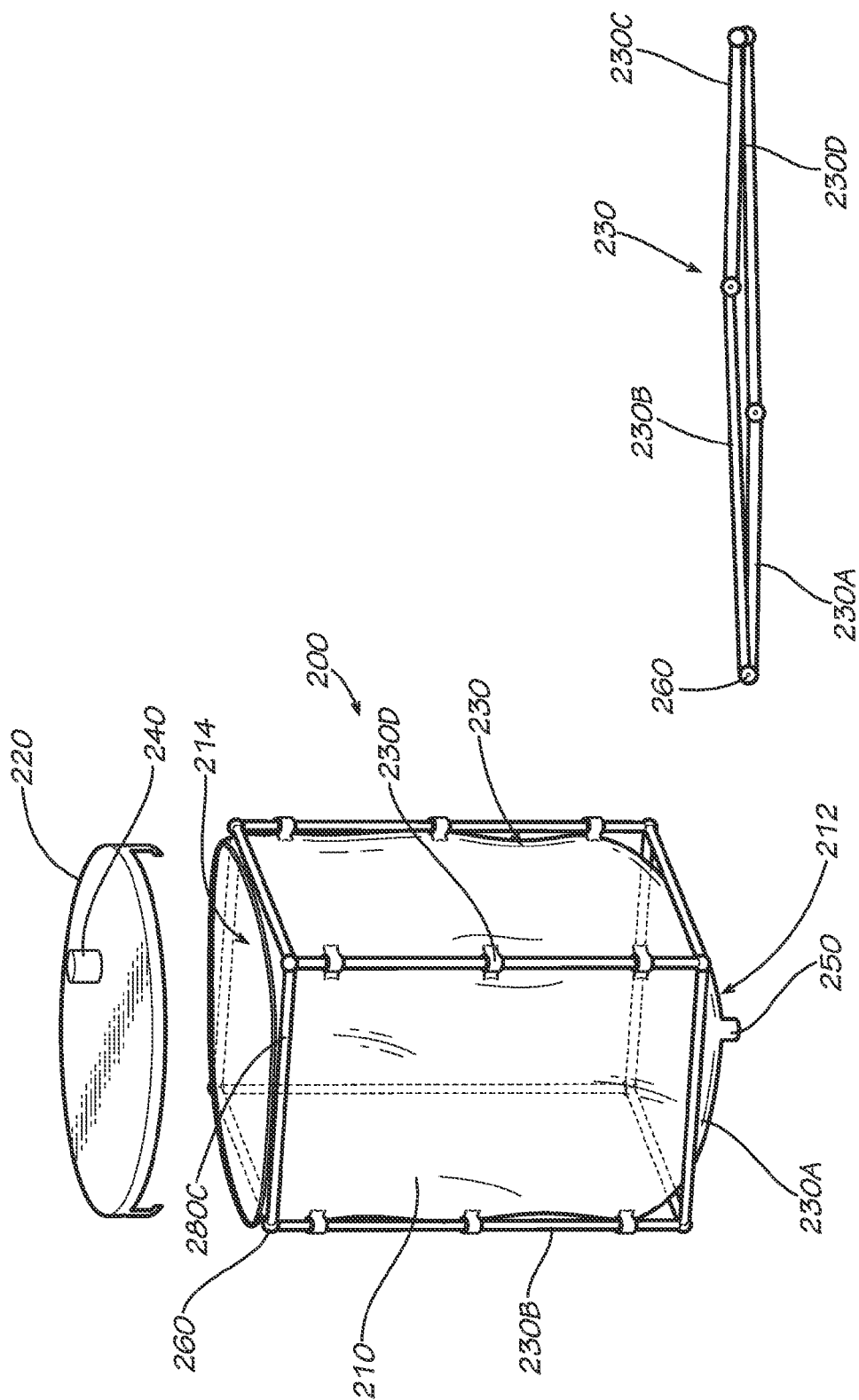

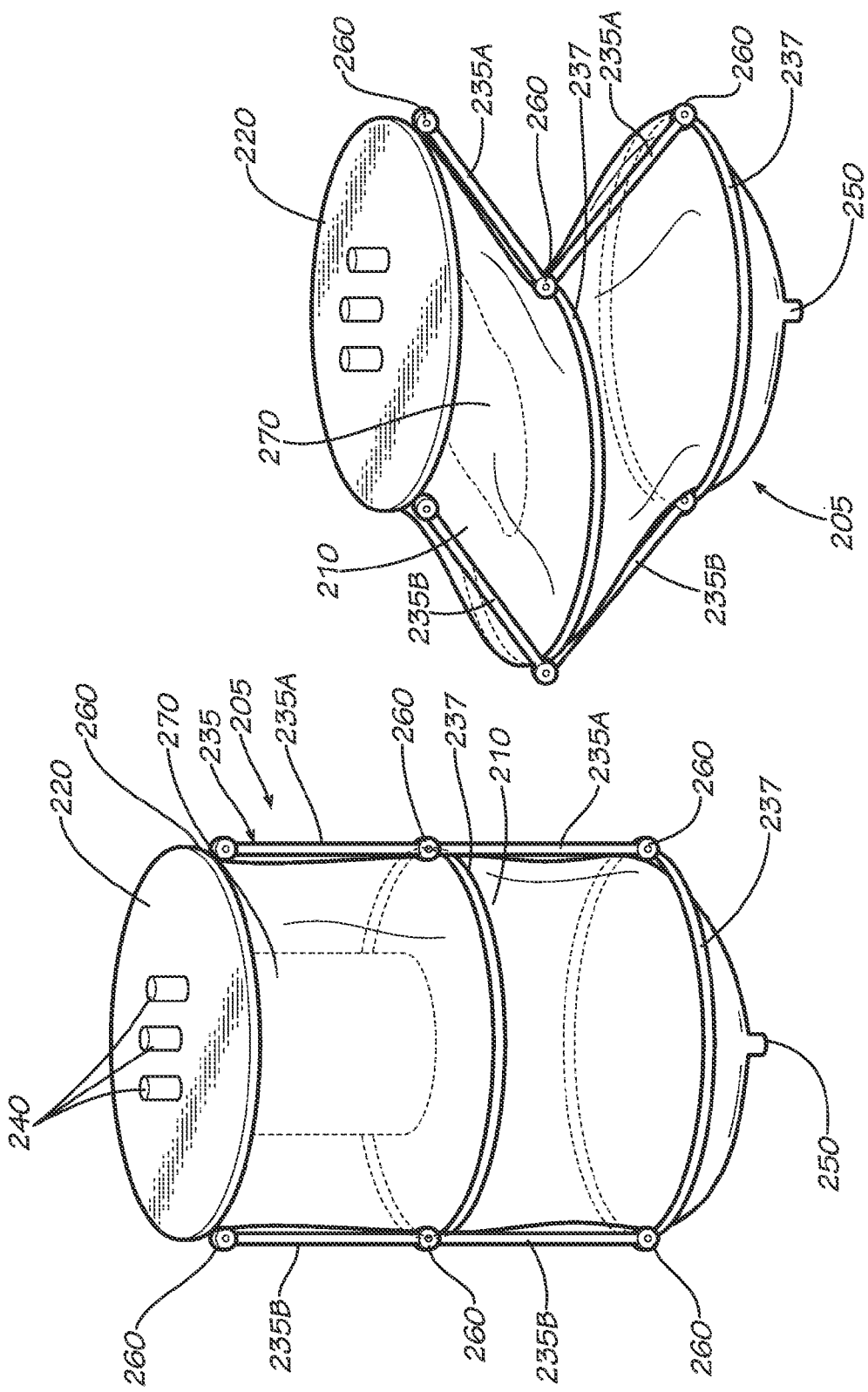

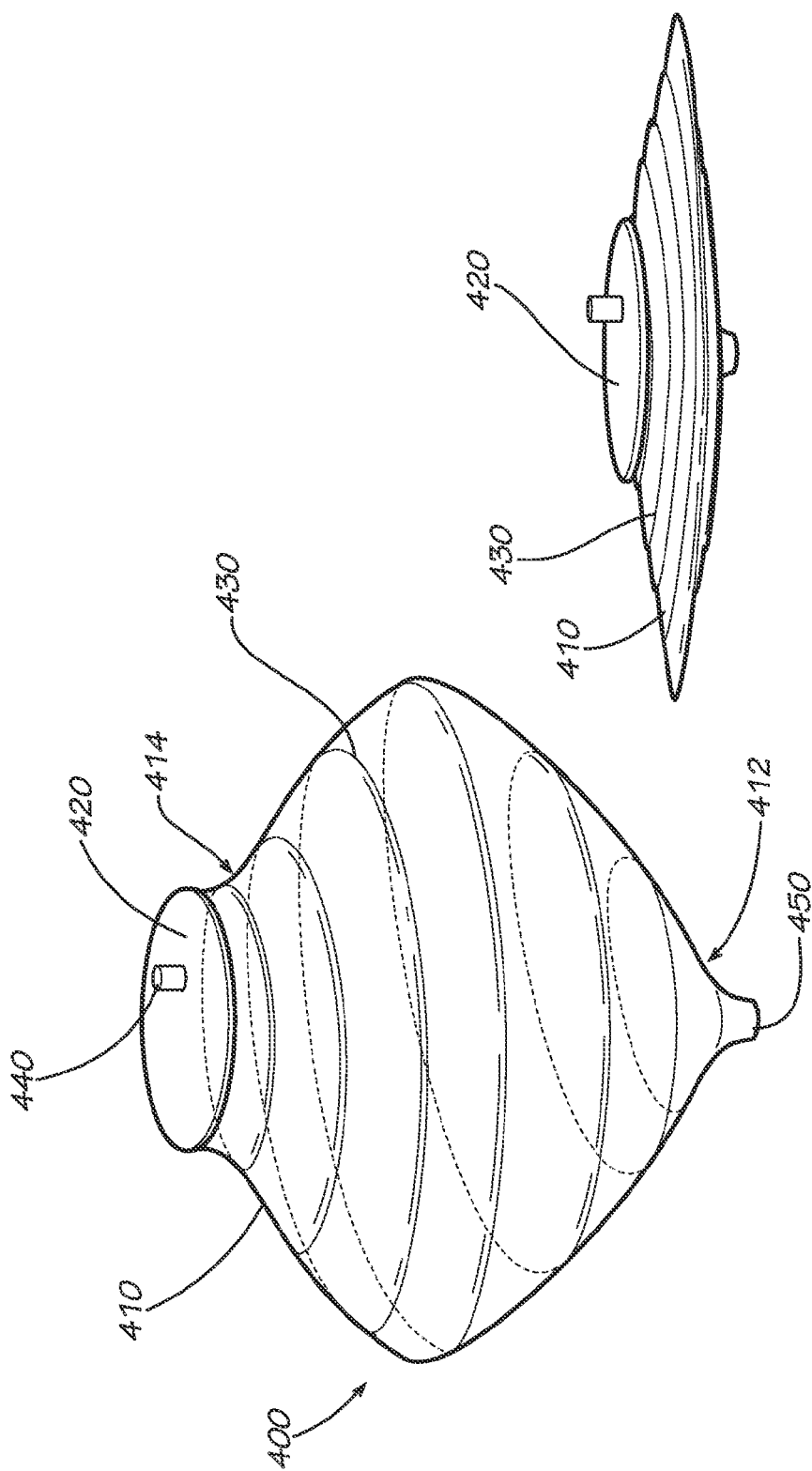

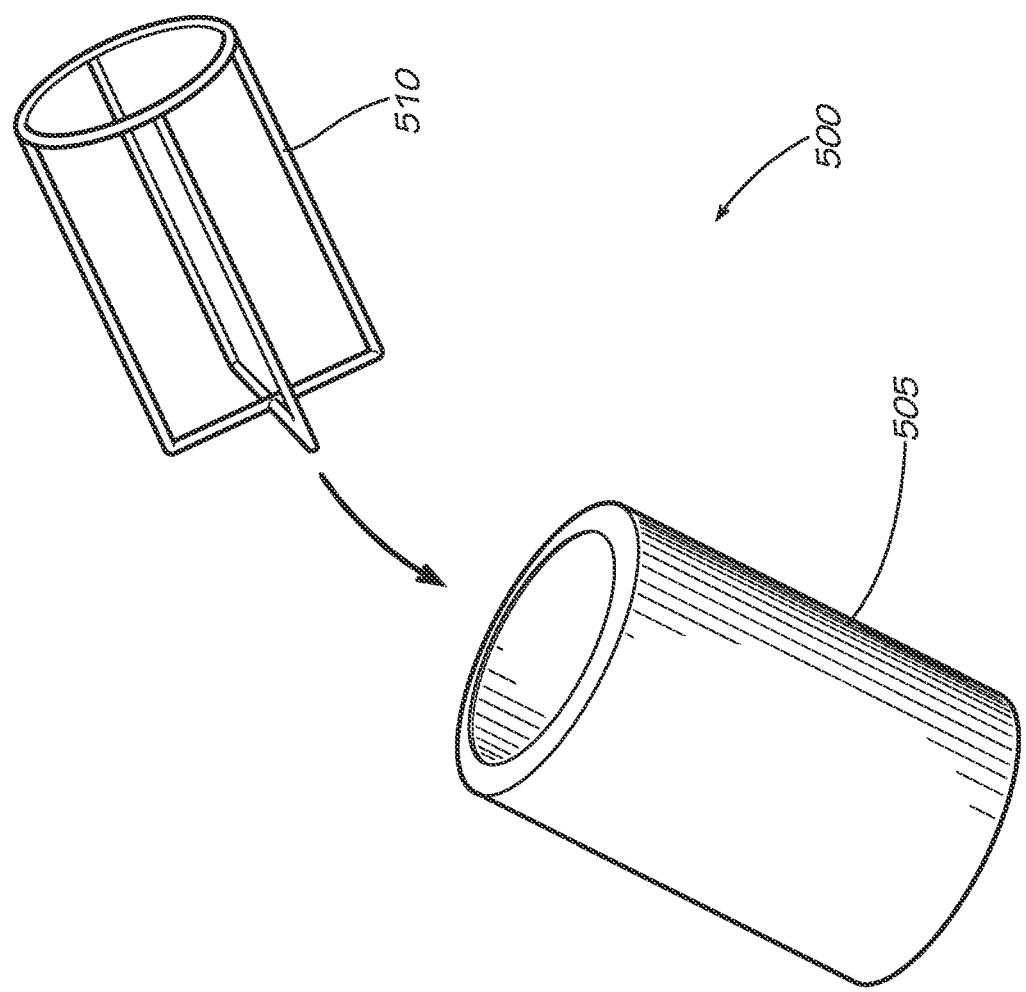

COLLAPSIBLE FLUID RESERVOIR

RELATED APPLICATION

This application claims priority to U.S. Provisional Application Ser. No. 61/116,911, entitled "Collapsible Fluid Reservoir," filed on Nov. 21, 2008, which is incorporated by reference as if fully set forth herein.

FIELD OF THE INVENTION

Embodiments described herein relate generally to fluid reservoirs, and more particularly to collapsible fluid reservoirs, which can be stored in a substantially flat or otherwise reduced profile configuration and expandable for use in containing and transferring biological fluids and other matter.

BACKGROUND OF THE INVENTION

During certain surgical procedures, such as cardiologic procedures, various fluid reservoir devices are used. For example, during cardiopulmonary bypass, cardiotomy reservoirs, venous reservoirs, arterial reservoirs, suction canisters, and the like, are used to contain blood at selected points throughout the circuit. Various reservoirs may serve to temporarily hold blood or other fluids, solids, or semi-solids, and may provide additional functions, such as oxygenation, filtration, air removal, and the like. Additionally, if used as a suction canister, a reservoir may have a vacuum line hooked to an external vacuum source to create a negative pressure within the reservoir, and a patient line of tubing and an end cannula piece for removing fluids, matter, etc., from a surgical site.

A simplified example extracorporeal circuit, such as may be used during cardiopulmonary bypass procedures, provides a cannula inserted into the patient's venae cavae and tubing coupling the cannula to a venous reservoir. From the venous reservoir, blood is pumped through one or more oxygenators, filters, and/or heat exchangers prior to delivery through an arterial cannula back to the patient. A cardiotomy reservoir may be used to receive blood suctioned from the surgical site and/or blood from within the extracorporeal circuit, such as from the venous reservoir, for additional filtering and gas removal. An arterial reservoir may be used to receive blood immediately prior to delivery to the patient, providing additional control over delivery flow rates and volume.

Reservoirs used as components in extracorporeal circuits, such as cardiotomy, venous, and/or arterial reservoirs, generally are either open circuit or closed circuit systems. Open circuit cardiotomy reservoirs are conventionally constructed as rigid reservoirs having a fixed size, shape, and volume. Open circuit reservoirs allow for the blood (or other biological fluid) to be in contact with air during use and are typically used as a passive drainage system, whereby gravity facilitates the fluid drainage into the reservoir. Open circuit cardiotomy reservoirs can reduce the amount of air in the venous line and can also compensate for varying or insufficient venous return levels. Rigid reservoirs used as open circuit cardiotomy reservoirs can be used in combination with vacuum augmented venous drainage, whereby a vacuum is applied to the rigid reservoir creating a negative pressure within to facilitate the venous drainage from the patient. Currently no collapsible means exist to allow for flat storage of any of the currently available open circuit, rigid reservoirs.

On the other hand, closed circuit reservoirs are typically made from flexible, non-rigid reservoir containers. Flexible containers can collapse when emptying, thus reducing the exposure of blood to air and preventing excess air from being pumped to the arterial side of the extracorporeal circuit and to the patient. Accordingly, most flexible containers are designed to collapse during use. However, currently available closed circuit, non-rigid reservoirs do not include an ability to expand the container and provide additional rigidity for use as a rigid or semi-rigid reservoir having a defined volume.

Fluid reservoirs can be constructed from disposable materials, such as from plastics or other polymers. While disposability presents many advantages, such as improving sterility and simplifying post-surgical cleaning, using disposable devices also requires storing and maintaining an increased inventory volume of the disposable devices. Thus, the physical size of the disposable devices may hinder the number of disposable devices kept in inventory and available on demand. Accordingly, limited size inventories may require frequent re-order and re-stocking, which may become impractical or increase costs. For example, rigid cardiotomy reservoirs may have a 3 Liter or larger capacity, thus taking up considerable space. Surgical suites and hospital stockrooms may be limited in their ability to stock large quantities of similar rigid reservoirs.

U.S. Pat. No. 4,443,220 describes a blood collection and transfer apparatus for use in autotransfusion. The apparatus of the '220 patent provides a collapsible bag with a stent adapted to hold it in distended form when desired, such as when a negative pressure is applied. However, the stent of the '220 patent has a circular base and a number of parallel tines extending upward from the base, over which loops of the bag may be placed. Thus, the stent of the '220 patent still presents the problem of unnecessarily occupying space during storage, because the stent cannot be collapsed or otherwise folded but is necessary for using the apparatus as a rigid or semi-rigid reservoir.

In another example, U.S. Pat. No. 5,935,093 describes a softshell cardiotomy reservoir. The apparatus of the '093 patent does not provide a rigid or semi-rigid reservoir with a defined volume to be used as an open system. Thus, while the softshell cardiotomy reservoir of the '093 patent may be collapsible, it is like any other non-rigid container, and cannot be used in place of a rigid container.

Accordingly, there exists a need for collapsible fluid reservoirs. There exists a further need for collapsible fluid reservoirs that collapse to a substantially flat configuration during storage and expand to define a volume during use as a rigid or semi-rigid reservoir.

SUMMARY OF THE INVENTION

Described is a collapsible fluid reservoir that may be expanded to a rigid or semi-rigid reservoir during use and then be collapsed to lie substantially flat when not in use. According to one embodiment, a collapsible fluid reservoir is provided. The collapsible fluid reservoir can include a substantially non-rigid container having a substantially open proximal end and a substantially sealed distal end opposite the proximal end defining a cavity therein, wherein the distal end includes at least one fluid outlet port extending therethrough. The collapsible fluid reservoir can also include a substantially rigid cap affixed to the proximal end of the non-rigid container and including at least one fluid inlet port extending therethrough and in fluid communication with the cavity.

In accordance with another aspect of this embodiment, the rigid cap may further include at least one vacuum port and/or a vent port extending therethrough and in fluid communication with the cavity. In one aspect, more than one fluid inlet port, and optionally one or more fluid outlet ports, may be included in the rigid cap. In certain aspects, one or more valves and/or filters may also be in fluid communication with the any of the fluid inlet ports and/or vacuum ports in the rigid cap.

In accordance with another aspect, the rigid cap may be removably affixed to the proximal end of the non-rigid container.

According to another example embodiment, a fluid container is provided. The fluid container includes a substantially non-rigid container comprising a substantially open proximal end and a substantially sealed distal end opposite the proximal end defining a cavity therein. The distal end can include at least one fluid outlet port extending therethrough. The open proximal end defines a cross-sectional shape adapted for affixing to a rigid cap.

According to one aspect of this embodiment, the cross-sectional shape of the open proximal end of the non-rigid container can be one of: circular, ovular, or polygonal.

According to yet another example embodiment, a collapsible fluid reservoir is provided. The collapsible fluid reservoir of this embodiment may include a collapsible frame, a substantially non-rigid container, and a substantially rigid cap. The collapsible frame is collapsible to a substantially flat configuration and expandable to a substantially expanded configuration defining a space within the collapsible frame. The substantially non-rigid container includes a substantially open proximal end and a substantially sealed distal end opposite the proximal end defining a cavity therein. The substantially non-rigid container may be positioned within the space of the collapsible frame and affixed to the collapsible frame at multiple connection points. The substantially rigid cap may be affixed to the proximal end of the non-rigid container and may comprise at least one fluid inlet port extending therethrough and in fluid communication with the cavity.

In accordance with one aspect of this embodiment, the collapsible frame may include multiple pivotably connected rigid frame members, wherein when the collapsible frame is collapsed to the substantially flat configuration, the plurality of rigid frame members lie in approximately a same plane. In accordance with another aspect of this embodiment, the rigid frame members may be removably connected.

According to an additional embodiment, a collapsible fluid reservoir is provided. The collapsible fluid reservoir of this embodiment includes a substantially non-rigid container having accordion-shaped walls, a substantially open proximal end, and a substantially sealed distal end opposite the proximal end defining a cavity therein, wherein the distal end comprises at least one fluid outlet port extending therethrough. The collapsible fluid reservoir further includes a substantially rigid cap affixed to the proximal end of the non-rigid container and including at least one fluid inlet port extending therethrough and in fluid communication with the cavity. The accordion-shaped walls of the non-rigid container are collapsible to a substantially flat configuration and expandable to a substantially expanded configuration defining a volume therein.

In accordance with one aspect of this embodiment, the collapsible fluid reservoir may further include at least one expanding member releasably attachable to the rigid cap and at least one point on an exterior surface of the non-rigid container between the proximal end and the distal end. The expanding member may have an adjustable length, wherein adjusting the length of the expanding member when attached to the substantially rigid cap and the non-rigid container adjusts the volume of the non-rigid container.

According to yet another example embodiment, a collapsible fluid reservoir is provided. The collapsible fluid reservoir of this embodiment includes a substantially non-rigid container constructed from substantially non-rigid material and including a substantially open proximal end and a substantially sealed distal end opposite the proximal end defining a cavity therein, wherein the distal end comprises at least one fluid outlet port extending therethrough. The collapsible fluid reservoir further includes a coil-shaped supporting member affixed to the non-rigid container at multiple points between the proximal end and the distal end of the non-rigid container, wherein the coil-shaped supporting member includes a proximal end, a middle section, and a distal end, and wherein the diameter of the coil-shaped supporting member increases from its proximal end to its middle section and decreases from its middle section to its distal end. The collapsible fluid reservoir further includes a substantially rigid cap affixed to the proximal end of the non-rigid container, which includes at least one fluid inlet port extending therethrough and in fluid communication with the cavity. The coil-shaped supporting member and the non-rigid container are collapsible to a substantially flat configuration and expandable to a substantially expanded configuration defining a volume therein.

According to yet another embodiment, a collapsible suction canister may be provided. The collapsible suction canister may include a non-rigid container, which includes a substantially open proximal end and a substantially sealed distal end opposite the proximal end defining a cavity therein. The collapsible suction canister may also include a substantially rigid cap affixed to the proximal end of the non-rigid container, wherein the substantially rigid cap includes at least one fluid inlet port extending therethrough and in fluid communication with the cavity, and at least one vacuum port.

According to one aspect of this embodiment, the substantially rigid cap may further include at least one fluid outlet port. According to another aspect of this embodiment, the substantially rigid cap may further include at least one of a filter or at least one valve in fluid communication with the vacuum port.

In accordance with various embodiments, a collapsible reservoir can serve as: (i) a cardiotomy reservoir, (ii) a venous reservoir, or (iii) an arterial reservoir.

Additional systems, methods, apparatus, features, and aspects are realized through the techniques of various embodiments of the invention. Other embodiments and aspects of the invention are described in detail herein and are considered a part of the claimed invention. Other features can be understood and will become apparent with reference to the description and to the drawings.

BRIEF DESCRIPTION OF THE DRAWINGS

The objects and advantages of the present invention will be better understood and more readily apparent when considered in conjunction with the following detailed description and accompanying drawings which illustrate, by way of example, embodiments of the collapsible reservoirs, and in which:

FIG. 2A illustrates an example collapsible reservoir in expanded configuration, according to one embodiment of the invention.

FIG. 2B illustrates an example support frame for a collapsible reservoir in collapsed configuration, according to one embodiment of the invention.

FIG. 2C illustrates an example collapsible reservoir in expanded configuration, according to one embodiment of the invention.

FIG. 2D illustrates an example collapsible reservoir in collapsed configuration, according to one embodiment of the invention.

FIG. 4A illustrates an example collapsible reservoir in expanded configuration, according to one embodiment of the invention.

FIG. 4B illustrates an example collapsible reservoir in collapsed configuration, according to one embodiment of the invention.

FIG. 5 illustrates an example filter, according to one embodiment of the invention.

DETAILED DESCRIPTION OF THE PREFERRED EMBODIMENTS

Figure 1A:
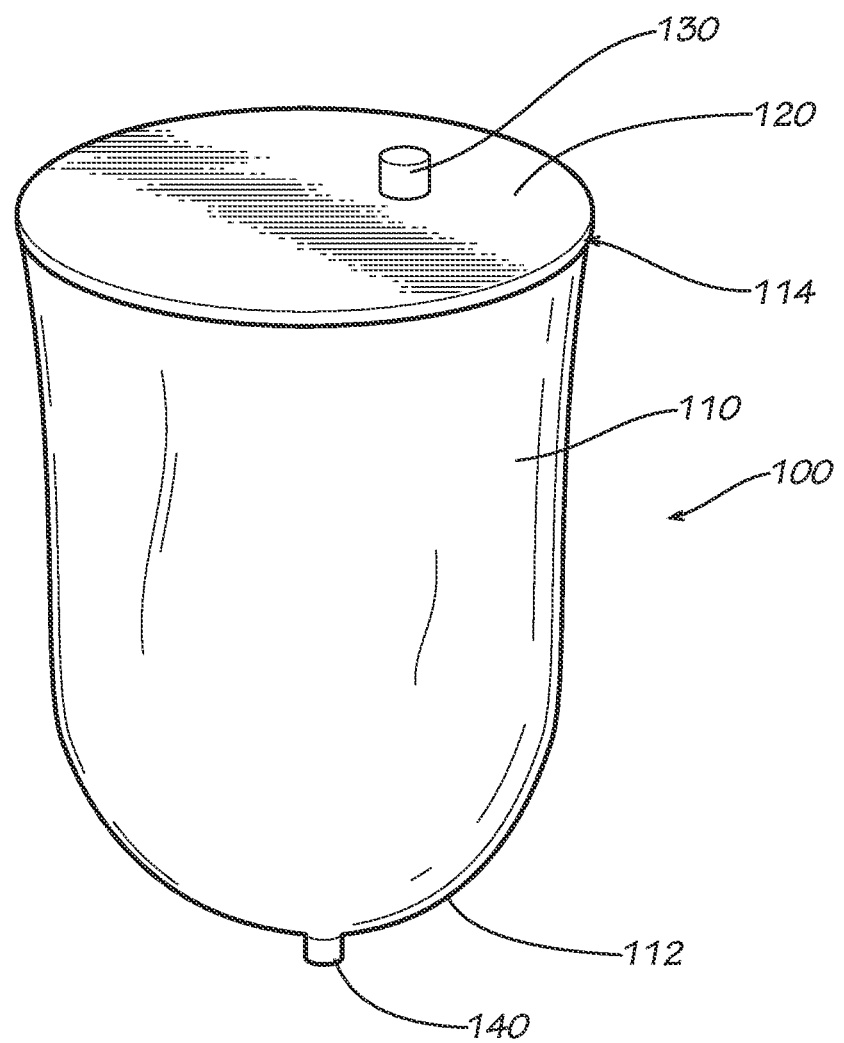
FIG. 1A illustrates an example collapsible reservoir in expanded configuration, according to one embodiment of the invention.

As required, detailed embodiments are disclosed herein; however, it is to be understood that the disclosed embodiments are merely exemplary, and the subject matter described may be embodied in various forms. Therefore, specific structural and functional details disclosed herein are not to be interpreted as limiting, but merely as a basis for the claims and as a representative basis for teaching one skilled in the art to variously employ that described in virtually any appropriately detailed structure.

The example collapsible reservoirs described herein provide space-conscious reservoirs for use during surgical procedures. The reservoirs described are collapsible, such that when stored the reservoirs occupy considerably less space than traditional rigid reservoirs. The reservoirs may be adaptable for use as any fluid container during medical treatment, such as, but not limited to, during cardiopulmonary bypass as described above, during blood infusion, and the like. Each reservoir includes at least a rigid cap and a non-rigid, collapsible container. The configuration of the non-rigid container may differ depending upon the intended use of the reservoir. The size and configuration of the non-rigid container may also differ depending upon the intended use, but may have up to or greater than a 5 Liter capacity in some embodiments, or as small as 500 mL capacity or even smaller in other embodiments. Various example reservoirs may further include additional support members to support the non-rigid container when in expanded configuration. The example reservoirs described herein may serve as traditional rigid reservoirs having a constant volume, or as semi-rigid reservoirs such that the volume of the collapsible container may be altered during use. Moreover, according to one example embodiment, a reservoir may include one or more fluid filters for filtering debris and other materials from the fluid flowing therethrough, which may optionally be collapsible.

According to one embodiment, the non-rigid containers are also collapsible to lie substantially flat, or at least to a reduced profile, and expandable to define a volume when in use. The non-rigid containers may be constructed from flexible, non-rigid materials, such as polymers like polyvinylchloride, having an open end and a closed end. The container may be foldable or otherwise collapsible for storage. The container may be constructed in any suitable configuration that would define the desired shape and volume of the container when expanded for use. For example, according to one embodiment, a non-rigid container may be formed as a single sheet using thermal forming techniques or blow molding techniques. According to another embodiment, however, the non-rigid container may be formed from two sheets (having any preformed shape) mated together at or near the edges, using any suitable mating technique, such as, but not limited to, solvent welding, radio frequency ("RF") welding, sonic welding, heat sealing, adhesives, and the like. The open end of the container may be permanently or removably sealed to the underneath side of the rigid cap, or may be sealed to the outer edge of the rigid cap. At least one fluid outlet port is integrated or otherwise provided proximate the closed end of the container and extends therethrough. Fluid can flow from within the container through the fluid outlet port into tubing connected to the outlet port. According to one embodiment, the closed end of the container can be formed to angularly converge to a point where the outlet port is provided, such that fluid contained within the container does not pool or gather along the bottom, but is gravity fed to the outlet port as a result of the angled or concaved bottom.

Example collapsible reservoirs include a rigid cap to which the non-rigid container is attached. The rigid cap assists in defining the open space and cross-sectional geometry of the container by defining the shape of the open end. The geometry of the rigid cap may vary, according to various embodiments described herein. For example, in one embodiment the rigid cap may have a substantially circular geometry, whereas in other embodiments the rigid cap may be more elongated, ovular, or elliptical in shape. In yet another embodiment, the rigid cap may be formed as a long, narrow cap, having a reduced width that is just wide enough to house one or more ports.

The rigid cap may also include one or more fluid inlet ports through which fluid may flow into the container. The configuration, number, and use of the one or more fluid inlet ports may vary depending upon the reservoir's intended use. For example, a collapsible reservoir used as a cardiotomy reservoir may include at least one fluid inlet port connectable to tubing delivering suctioned fluid from the surgical site into the reservoir. In another example, a collapsible reservoir used to hold blood (or other fluid) prior to infusion to a patient may include one or more fluid inlet ports connectable to one or more external blood supply containers. The rigid cap may also include one or more venting ports for venting air from within the container, one or more vacuum ports for applying a suction to the container, one or more additional fluid ports for adding fluid or other substances to the container, such as anticoagulant, and/or one or more fluid outlet ports. Any number of fittings may be used to provide a fluid inlet, vent, or vacuum port, such as, but not limited to, barbed fitting, female/male luer loc fitting, straight fitting, relief valve, one-way valve, and the like. The selection of the fitting will depend upon the intended use of the port. For example, a relief valve or one-way positive check valve may be used as a venting port, whereas a barbed fitting or female luer loc fitting may be used as an inlet port. According to one embodiment, the rigid cap may also have one or more fluid filters for filtering debris and other materials from the fluid flowing therethrough. A filter may also be collapsible.

An example collapsible reservoir serving as a suction canister during surgical procedures may be operable with a means for creating a negative pressure within the reservoir and a fluid inlet port for suctioning fluid from a patient's surgical site. Embodiments configured for or used as a suction canister may have a rigid cap that includes one or more vacuum ports connectable to an external vacuum source, and one or more fluid inlet ports connectable to patient tubing and suction cannulae. Moreover, in example embodiments, the rigid cap may include one or more filters in communication with the vacuum port, preventing debris, such as microorganisms, from escaping the reservoir and entering the vacuum line. Similarly, example embodiments may further include one or more valves, such as a two-way or multi-way shut-off valve, or any other suitable means for restricting air flow and/or fluid flow, in communication with the vacuum port. For example, a relief valve or negative check valve may be provided that is configured to actuate open upon application of a predetermined negative pressure.

In some example embodiments, additional support members may also be included to support the non-rigid container when in expanded configuration. For example, the support members may be affixed to multiple points on the exterior surface of the non-rigid container, such that when the support members are expanded they positively expand the non-rigid container to assist in defining the form, shape, and rigidity of the container during use. These support members may be collapsible or otherwise deconstructed to also lie in a substantially flat configuration, or have a reduced profile, when not in use. In one example, the support members may be configured as a frame of pivotably connected members that, when expanded, lock together to form a three-dimensional shape, such as a cube, a cone, a pyramid, or the like. In similar embodiments, the support members may be constructed as solid or substantially interlocking solid panels that when locked in an expanded configuration form the three-dimensional shape. In another example, the support members may be one or more adjustable support arms that are attachable to the rigid cap and to one or more points on the exterior surface of the non-rigid container, providing a tension to expand the non-rigid container in a direction away from the rigid cap. Any other suitable configuration of rigid support members that are collapsible and expandable to support the non-rigid container may be used with any of the example embodiments of collapsible fluid reservoirs described herein.

In some versions, support members of example collapsible reservoirs provide enough rigidity and integrity to withstand significant negative pressures, such as may be applied by suction when used as a cardiotomy reservoir, without collapsing or otherwise undergoing substantial deformation. For example, the support members may include locking mechanisms operably associated with joints and/or attachment points to prevent them from collapsing or pivoting when in an expanded configuration, while allowing them to collapse when desired to package, store, ship, or dispose of the reservoirs. The support members may be further reinforced by circumferential members providing additional lateral stability, or other reinforcing members positioned within the support frame. Moreover, the non-rigid container can be affixed to the support frame in a manner, such as by loops, clips, heat sealing, adhesive, etc., as described more fully below, to resist the forces created by negative pressure which may otherwise cause the container to separate from the support frame and collapse inward. Another way to prevent collapse or undesired deformation is to stretch the non-rigid container over the support frame, such that the force created by the negative pressure forces the non-rigid container against the support frame, thus eliminating the need for stronger means for affixing the container to the frame. Various suitable reservoir configurations may be employed to reduce the impact negative pressure may have on the container, as is described more fully herein, and will be apparent in light of that described and illustrated herein.

Accordingly, collapsible reservoirs may be used as any number of reservoir types during surgical procedures or other medical treatment. Moreover, the collapsible reservoirs can collapse to a substantially flat or reduced profile configuration when not in use, including the rigid cap, the collapsible non-rigid container, and optionally collapsible support members. According to various embodiments, the collapsible reservoirs can be collapsed to a collapsed configuration having a height less than approximately 20 percent of the height when in its expanded configuration, and in some embodiments as little as 10 percent or even 1 percent of its height when in its expanded configuration. Depending upon the expanded size and/or volume of the non-rigid container, the collapsible reservoirs may collapse to as little as ½ inches to 1 inches in height, measured from one side of the rigid cap to the opposing side of the non-rigid container, and in some embodiments at least less than 6 inches or at least less than 2 inches in height. It is appreciated that the relative percentage of the reduced profile and the overall height when collapsed depend in part on the configuration of the collapsible reservoir, including the height of the rigid cap and whether any additional structural members are included. For example, in one embodiment a collapsible reservoir having a capacity between approximately 3 L and 3.5 L may collapse from an expanded configuration of 15 inches to a collapsed configuration of between 1 and 2 inches. The non-rigid container, however, itself may be formed to collapse to have minimal profile, which may be as little as ¹⁄₃₂ inches, according to one embodiment, or as little as ¹⁄₁₆ or ¼ inches in other embodiments. It is appreciated that these dimensions and relative dimensions are provided for illustrative purposes, and that in some embodiments, the ratios may be greater or less, depending upon the configuration of the device and/or its intended use. In addition, any of the non-rigid containers may be formed with pre-formed creases, folds, pleats, or other patterns that assist collapsing the non-rigid container in its most reduced profile.

The collapsible reservoirs may be distributed in substantially flat sterile packs, which may be stacked or otherwise stored in a space-efficient manner prior to use. Furthermore, after use, the reservoirs may be similarly collapsed, thus reducing the volume occupied and the associated costs incurred for reservoir disposal.

Turning now to a discussion of the drawings, the collapsible reservoir may be further understood with reference to FIGS. 1-5, providing example, non-limiting embodiments.

FIG. 1 illustrates an example embodiment of a collapsible reservoir. An example collapsible reservoir 100 is illustrated in expanded configuration, which includes a non-rigid container 110 and a rigid cap 120 attachable to the proximal end of the non-rigid container 110. The non-rigid container 110 includes a substantially sealed distal end 112 and a substantially open proximal end 114, defining a volume in which blood or other fluids may be contained.

The non-rigid container 110 may be constructed of any flexible, durable material suitable for containing biological fluids, such as blood or other material. In one example embodiment, the non-rigid container 110 is constructed from polyvinylchloride; though, any other suitable material may be used. The non-rigid container 110 may be molded from a single sheet in the desired shape and size, such as using thermal forming techniques or blow molding techniques. In other embodiments, however, the non-rigid container 110 may be formed from multiple sheets and sealed together in the desired shape and size, such as by solvent welding, RF welding, sonic welding, adhesive, and/or heat sealing. In one example embodiment, the non-rigid container 110 is constructed from multiple layers, providing additional strength and protection against puncturing, the mass of the fluid or other material contained therein, increased temperatures, etc.

One or more fluid outlet ports 140 may be formed in or otherwise integrated with the distal end 112, or proximate the distal end 112, of the non-rigid container 110, operably connectable to tubing to drain fluid from within the container. The fluid outlet port 140 may be configured as a fitting to accept typical surgical tubing. In one example, the fluid outlet port 140 may be constructed as a rigid fitting extending through the distal end of the non-rigid container 110 and having an external diameter that gradually tapers, and optionally including a hose and barb fitting that provides convenient connection for various tubing diameters to slide thereover. In example embodiments in which the non-rigid container 110 is used to retain fluids, the one or more fluid outlet ports 140 may further include a valve, such as a two-way or multi-way shut-off valve, or any other suitable means for selectively restricting fluid flow from the container. In another embodiment, such as those serving as a suction canister, the non-rigid container 110 may not have a fluid outlet port at its distal end 112, but may instead be sealed such that it is fluid impervious. Further, as shown in FIG. 1A, one embodiment of the non-rigid container 110 is formed to have a concave or gradually sloping bottom sloping toward the location of the fluid outlet port 140 to prevent pooling of fluid along the bottom and to promote fluid flow through the fluid outlet port 140.

The collapsible fluid reservoir 100 includes a rigid cap 120 connected to the proximal end of the non-rigid container 110. The rigid cap 120 may be constructed of any rigid or substantially rigid material, such as from rigid polymers. The rigid cap 120 is attachable to the non-rigid container 110 to seal or substantially seal the container and the cap, providing a volume into which fluids may be delivered. In one example embodiment, the open proximal end 114 of the non-rigid container 110 is permanently sealed to the rigid cap 120, either underneath the edge or lip formed around the circumference of the rigid cap 120, or to the outside of the rigid cap 120 along its circumference. The non-rigid container 110 can be permanently sealed using any number of known techniques, such as, but not limited to, solvent welding, RF welding, sonic welding, heat sealing, adhesives, and the like. In another example embodiment, the non-rigid container 110 may be removably attached to the rigid cap 120, for example, by having a diameter slightly smaller than the rigid cap 120 diameter and stretching over the edges of the rigid cap 120. In yet other embodiments, the rigid cap 120 may include a rubber o-ring and threaded retainer ring which would secure the non-rigid container 110 to the rigid cap 120. It is appreciated that other means for connecting, either permanently or removably, the non-rigid container 110 to the rigid cap 120 may be used.

The shape of the rigid cap 120 may vary, according to the desired size and shape of the non-rigid container 110 and the intended purpose. The embodiment shown in FIG. 1A includes a rigid cap 120 having a substantially circular shape. However, it is appreciated that a rigid cap 120 may be formed according to any number of other geometries, such as elliptical, polygonal, elongated, and the like. FIGS. 1B-1E illustrate additional example rigid cap 120 geometries.

The rigid cap 120 includes at least one fluid inlet port 130 through which fluid may be delivered into the non-rigid container 110. The fluid inlet port 140 may be configured as a fitting to accept typical surgical tubing as may be used for the reservoir's intended use. In one example, the fluid inlet port 130 may include a fitting extending from the rigid cap 120 and having an external diameter that gradually tapers, and optionally including a hose and barb fitting that provides convenient connection for various tubing diameters to slide thereover. Other fittings include, but are not limited to, barbed fitting, female/male luer loc fitting, straight fitting, relief valve, one-way valve, and the like. Although the fittings are illustrated herein as extending in an approximately vertical direction from the rigid cap 120, it is appreciated that in other embodiments, one or more fittings may extend in a different direction, such as at an angle relative to the cap, extending in an approximately horizontal direction (e.g., 90 degrees different than that shown herein), and or in any other direction as may be desired to accommodate anticipate inlet and/or outlet connections. As described above, the rigid cap 120 may additionally include multiple fluid inlet ports 130 of varying sizes, depending upon the reservoir's intended use, such as a larger fluid inlet port that may function to deliver additives and/or non-fluid materials to the container. In example embodiments, each fluid inlet port 130 may include a removable cap that allows for the port to be sealed when not in use, providing additional flexibility in the varying uses of a single rigid cap 120 design. The rigid cap 120 may also include one or more vent ports to allow air to pass through the cap and into or out of the collapsible reservoir 100. In example embodiments including a vent port, a removable cap may also be included to seal the vent port when not desired. In another embodiment, a vent port may be configured as a one way relief valve or positive check valve that is designed to actuate into an open position under a predetermined amount of pressure. The example embodiment illustrated in and described with reference to FIGS. 1B-1E, 2C, and 2D includes a rigid cap having multiple ports, which may be any combination of one or more fluid inlet ports, vacuum ports, or vent ports.

In example embodiments, the rigid cap 120 may additionally include at least one vacuum port for connecting to an external vacuum source, allowing the generation of a negative pressure within the non-rigid container 110, such as may be performed when used as a suction canister whereby the negative pressure creates a suction force through one or more fluid inlet ports 130. Embodiments including a vacuum port may further optionally include at least one valve mechanism for operably restricting flow through the vacuum port and/or at least one filter for filtering debris or other matter from entering the vacuum line. The valve mechanism may be any other suitable means for restricting air flow and/or fluid flow, such as a one-way relief valve, negative check valve, or a two-way or multi-way shut-off valve. The valve mechanism may be integrated with the rigid cap 120, on its top side, underneath side, or a combination thereof, or may be removably attachable to either the vacuum port or vacuum tubing. In one embodiment the valve mechanism may additional serve as the vacuum port. In one example, the filter may be similar to that described and illustrated with reference to FIG. 5 with smaller dimensions compatible with the vacuum port. In other embodiments, however, any other suitable filter may be provided. Like the valve mechanism, the filter may be integrated with the rigid cap 120, on its top side, underneath side, or a combination thereof, or may be removably attachable to either the vacuum port or vacuum tubing.

Different from other example embodiments described below, other than the rigid cap 120, this example collapsible reservoir 100 does not include any additional means to support the non-rigid container 110. Accordingly, this collapsible reservoir 100 may be used as a semi-rigid or non-rigid reservoir during certain medical procedures. However, according to other example embodiments, the collapsible reservoir 100 illustrated in any of FIGS. 1A-1E can be modified to include one or more support members to provide structural support and integrity to the non-rigid container 110, such as any of the additional embodiments described in more detail herein. For example, according to one embodiment, the collapsible reservoir 100 illustrated in any of FIGS. 1A-1E can include members similar to those shown in and described with reference to FIGS. 3A and 3B.

The collapsible reservoir 100 is collapsible to a substantially flat configuration simply by allowing the non-rigid container 110 to fold or otherwise collapse flat. Accordingly, as described with other example embodiments, the collapsible reservoir 100 may be distributed in sealed plastic in collapsed form such that the non-rigid container 110 is collapsed and lying substantially flat with, or proximate to, the rigid cap 120. Thus, prior to use, a greater number of collapsible reservoirs 100 may be stored in flat configuration, occupying less space than traditional rigid reservoirs. In one embodiment, the non-rigid container 110 is simply collapsed without following any predefined pattern; though, in other embodiments, the non-rigid container 110 may be rolled, folded, etc., according to a predefined pattern.

Figure 1B:
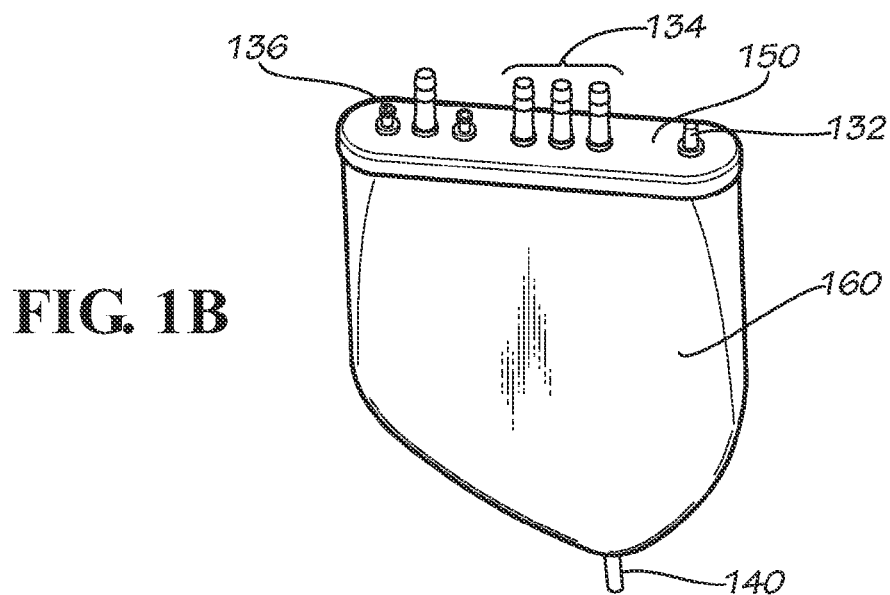
FIG. 1B illustrates an example collapsible reservoir in expanded configuration, according to one embodiment of the invention.
Figure 1C:
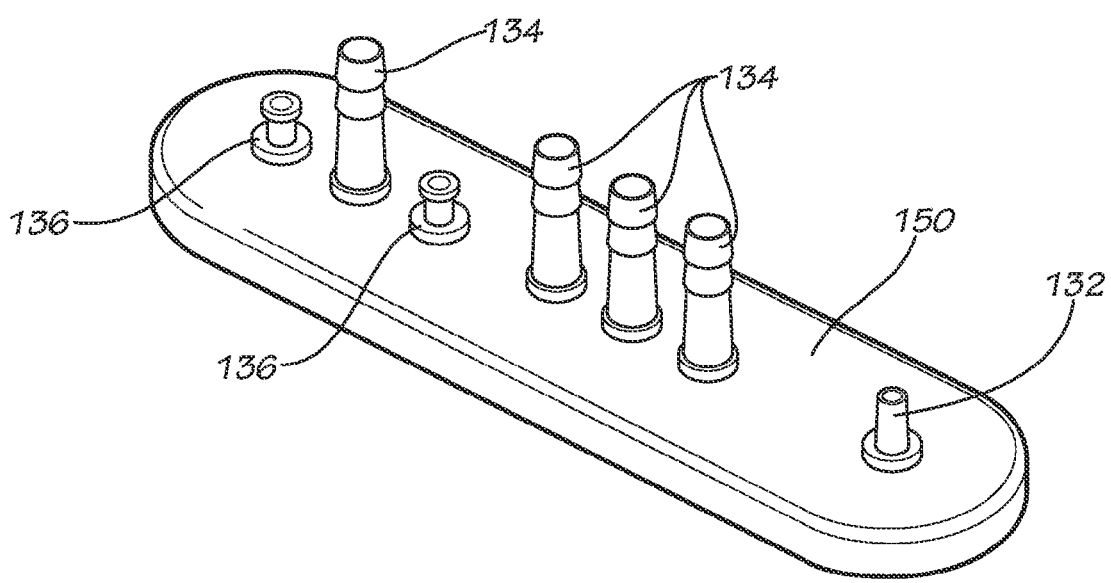
FIG. 1C illustrates an example rigid cap, according to one embodiment of the invention.
Figure 1D:
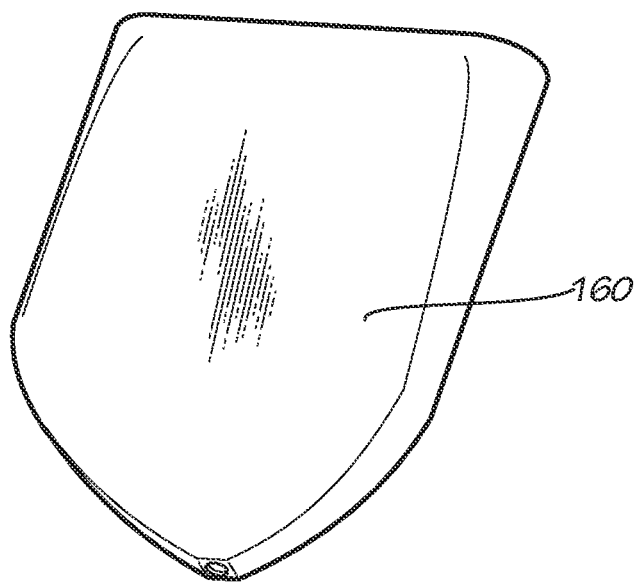
FIG. 1D illustrates an example non-rigid container, according to one embodiment of the invention.

FIGS. 1B-1E illustrate other example embodiments of a collapsible reservoir, each including a rigid cap or other rigid member and a non-rigid container. With reference to FIGS. 1B-1D, the non-rigid cap 150 is shown as having a substantially elliptical geometry—longer than it is wide. This geometry may further reduce packaging and storage space, as well as provide a narrower profile when in use. The non-rigid container 160 of this embodiment is illustrated as being formed from a single sheet (e.g., thermally formed), and affixed to the underneath side of the rigid cap 150. However, it is appreciated that any other technique may be used to form a non-rigid container, such as two mated sheets (e.g., solvent welded, RF welded, sonic welded, heat sealed, or using adhesive). The fluid outlet port 140 can be integrated within the bag at the time of manufacturing (e.g., when thermally forming a single piece or mating two sheets), or at some point after forming the container but before use (e.g., the fitting applied into a aperture formed in the container).

The rigid cap 150 of this embodiment is illustrated as having at least three different types of ports passing therethrough, and including multiple ports of the same kind For example, a vent port 132 is illustrated, which may be a simple straight port with a straight fitting, or may include a valve mechanism as described above. In other embodiments, any other port types described herein may serve as a vent port, such as if included with a cap or always remaining open. Multiple fluid inlet ports 134, 136 are shown, inlet ports 134 being configured as a hose and barb fitting and inlet ports 136 being configured as a female luer loc fitting. It is appreciated that, according to various embodiments, any number of ports in any number of configurations can be included with a rigid cap.

Figure 1E:
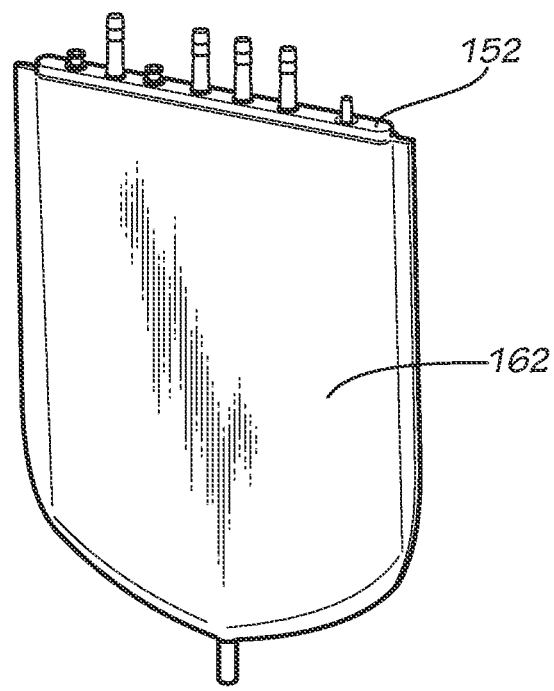
FIG. 1E illustrates an example collapsible reservoir in expanded configuration, according to one embodiment of the invention.

FIG. 1E illustrates another example embodiment of a collapsible reservoir 100 having an elongated rigid cap 152 and a non-rigid container 162. The elongated rigid-cap 152 of this embodiment is formed as an elongated, narrow member with just enough area to retain one or more ports (e.g., any of the inlet, vent, or vacuum ports and associated fittings described herein). In one embodiment, the rigid cap may be at least approximately 20 times longer than it is wide; though, in other embodiments it may be at least approximately 10 times longer than it is wide, or at least approximately 5 times longer than it is wide. For example, according to one embodiment in which the non-rigid container 162 has a capacity of approximately 700 mL, the length of the elongated rigid cap 152 is approximately 13 to 15 times its width. It is appreciated that these relative dimensions are provided for illustrative purposes, and that in some embodiments, the ratios may be greater or less, depending upon the configuration of the device and/or its intended use. The elongated rigid cap 152 is formed in such a narrow configuration to further reduce the profile of the collapsible reservoir when in use and for storage and packaging.

The non-rigid container 162 of this embodiment is illustrated as being formed from two sheets mated together using any suitable techniques, such as, but not limited to, solvent welding, RF welding, sonic welding, heat sealing, adhesive, and the like. According to this embodiment, the non-rigid container 162 is affixed to the rigid cap 152 by stretching and securing the proximal end of the container 162 over the outside edge of the rigid cap 152. One reason for securing the non-rigid container 162 in this manner is to provide the largest opening of the container 162 while still reducing the profile of the entire device. Another reason is to avoid interference by the seams extending along the edge of the non-rigid container 162 with the cap 152, which may occur if affixed to the interior edge of the rigid cap 152. However, it is appreciated that any means described herein or otherwise known can be used to affix the non-rigid container 162 to the rigid cap 152 of this embodiment.

While the collapsible reservoir configurations illustrated in and described with reference to FIGS. 1A-1E are described as not including any additional support members, it is appreciated that similar reservoir configurations can further include any of the support members and other structural aspects further illustrated in and described with reference to FIGS. 2-5 below.

FIG. 2A illustrates an example collapsible reservoir 200 in expanded configuration, according to one embodiment of the invention. This example reservoir includes a non-rigid container 210 within a rigid or substantially rigid support frame 230 and a rigid cap 220 attachable to the top of the rigid support frame 230 and/or the non-rigid container 210. The non-rigid container 210 includes a substantially sealed distal end 212 and a substantially open proximal end 214, defining a volume in which blood or other fluids or materials may be contained.

The example embodiment illustrated in FIG. 2A includes a support frame 230 constructed from a plurality of rigid support members 230A-230D configured in a three-dimensional rectangular-shape (which includes a cube). The rigid support members 230A-230D may be constructed from any rigid or substantially rigid material, such as from rigid polymers, metal, or the like. In this example embodiment, the rigid support members 230A-230D are pivotably attached to each other by hinges 260 at their distal ends so they may pivot with respect to each other to the collapsed configuration, as is illustrated in FIG. 2B. Comparing FIG. 2A to FIG. 2B to illustrate pivoting to collapse the support frame 230, parallel support members 230A and 230C, which are attached to parallel support members 230B and 230D and form a rectangular shape when expanded, pivot at hinges 260 such that support members 230C and 230B straighten to extend in a substantially straight line with respect to each other and lie against support members 230D and 230A, respectively, which also extend in a substantially straight line with respect to each other. Though not illustrated, the opposite support members not numbered collapse in the same manner. Accordingly, as illustrated in FIG. 2B, in collapsed configuration, the support frame 230 lies in a substantially flat configuration such that each of the support members 230A-230D lie adjacent each other. To expand, the support members 230A-230D are pivoted at hinges 260 in the opposite direction, such that support members 230A and 230C lie approximately parallel to each other and at approximate right angles to support members 230B and 230D. In example embodiments, hinges 260 may include locking mechanisms, such as by increased friction or tension screws, to maintain the support frame 230 in expanded configuration.

As illustrated in FIG. 2A, the non-rigid container 210 is positioned within the support frame 230. The non-rigid container 210 may be permanently attached to the support frame 230 at multiple connection points, such as by heat sealing or by adhesive during manufacture, or may be removably attached, such as by clips, loops, adhesive, or the like. The support frame 230 expands and provides lateral support to the non-rigid container 210 when in use. Accordingly, the support frame 230 can withstand the full weight of a fluid filled non-rigid container 210. Similarly, the support frame 230 and its attachment to the non-rigid container 210 can provide sufficient rigidity and strength to withstand the application of negative pressures, which may be as much as approximately −100 mmHg to −300 mmHg, to the container, such as may be applied when used as a cardiotomy reservoir. In one example embodiment, the collapsible reservoir 200 may further include a bottom support member (not illustrated) providing support to the distal end 212 of the non-rigid container 210. The bottom support member may be integrated with the support frame 230, or may be positioned to rest on the bottom support member 230A. The bottom support member may be configured as a frame constructed from one or more members, a basket, a substantially solid piece having an orifice through which the fluid outlet port 250 may extend, or the like.

In some example embodiments that include a support frame 230, the rigid cap 220 may include pressure tabs, clips, or other means for removably attaching the rigid cap 220 to the support frame 230. In another example, the rigid cap 220 may be permanently attached to the support frame 230, simplifying assembly and adding additional strength to the support frame 230.

The collapsible reservoir 200 illustrated in FIGS. 2A and 2B may be distributed in sealed plastic in collapsed form such that the non-rigid container 210 lies substantially flat with the rigid cap 220 or otherwise has a significantly reduced profile.

Though not illustrated in FIGS. 2A and 2B, the support frame 230 may be configured in shapes other than a three-dimensional rectangular-shape, such as conical, pyramidal, semi-spherical, or the like, with altered configurations of support members and hinges. The support frame 230 may also optionally include one or more members providing additional reinforcement to the structure when in expanded configuration, such as diagonal or crossed supports between support members 230A-230D. In another example, rather than being pivotably connected by hinges 260, the support members may removably connect to each other to create the desired shape, such that in a collapsed configuration, the support members are pulled apart for flat storage. In another example, the support frame 230 is constructed from multiple solid panels, which may be pivotably and/or removably connected, instead of individual members as illustrated in FIGS. 2A and 2B. It is appreciated that many other configurations and means for connecting, collapsing, and expanding a support frame 230 may be employed to provide additional support to the non-rigid container 210.

For example, FIGS. 2C and 2D illustrate another example embodiment that includes a non-rigid container supported by a support frame; however, the support frame is configured in a different manner from that illustrated in FIGS. 2A and 2B. More specifically, FIG. 2C illustrates an example collapsible reservoir 205 in expanded configuration, according to one embodiment of the invention. This example reservoir includes a non-rigid container 210, including at least one fluid outlet port 250, similar to that illustrated and described above with reference to FIG. 2A, with a rigid or substantially rigid support frame 235 including one or more rigid or substantially rigid circumferential supports 237. The support frame 235 may be configured as one or more support members 235A-N extending in an approximate distal direction from a rigid cap 220 to at least partially support the non-rigid container 210. One or more circumferential supports 237 may be positioned in one or more planes distal the rigid cap 220 and between one or more of the support members 235A-N, providing lateral support for the support frame 235 and the non-rigid container 210, such as may be used to prevent the non-rigid container 210 from collapsing when subjected to a negative pressure. As illustrated in FIG. 2C, in one example embodiment, at least two support members 235A, 235B extend from the rigid cap 220 and have at least two circumferential supports 237 configured in a ring shape having approximately the same or similar diameter as the rigid cap 220, and defining a space through the middle to allow the non-rigid container 210 be positioned therein. It is appreciated, however, that the support members 235A-N and/or the circumferential supports 237 are not limited to the geometries illustrated in FIGS. 2C and 2D. For example, support member circumferential supports may define a square-shaped cross section, a triangle-shaped cross section, any other polygonal-shaped cross section, an ovular-shaped cross section, and the like.

The non-rigid container 210 may be suspended from within the support frame 235 (as illustrated), or stretched or otherwise positioned over the support frame 235. For embodiments in which the non-rigid container is suspended from within the support frame 235, the non-rigid container 210 may be permanently attached to the support frame 235 at multiple connection points, such as by heat or adhesive during manufacture, or removably attached, such as by clips, loops, adhesive, and the like.

Moreover, the support members 235A-N may optionally include one or more hinges 260 that allow the support frame 235 to collapse in a substantially flat configuration or a reduced profile, similar to that described with reference to FIGS. 2A and 2B. As illustrated in FIG. 2C, in one example embodiment, hinges 260 may be placed at or near the rigid cap 220 and/or at or near the position of the circumferential supports 237. However, it is appreciated that any number of hinges 260 may be included in numerous configurations. FIG. 2D illustrates an example of the collapsible reservoir 205 in a partially collapsed configuration as compared to FIG. 2C. As shown, the support member 235A may pivot at the hinges 260 such that it folds in two, bringing the rigid cap 220 toward the lower circumferential support member 237. Similarly, the additional support member 235B may also fold in two at the hinge 260 in the same manner. The support frame 235 may continue to fold into a flat or substantially flat configuration, for ease of packaging, shipping, storing, or disposal, as described in more detail above. In example embodiments, the hinges 260 may include locking mechanisms, such as by increased friction or tension screws, to maintain the support frame 235 in expanded configuration.

In another example embodiment, the support members 235A-N may be removably attached to the rigid cap 220 and/or the circumferential support members 237, to allow for efficient construction, assembly, shipping, storage, and/or disposal.

The rigid cap 220 as illustrated in FIGS. 2C and 2D optionally includes a plurality of multiple fluid inlet ports 240 of varying sizes, depending upon the reservoir's intended use, as described in more detail with reference to FIGS. 2A and 2B. In other embodiments, one or more of the ports may be vacuum ports, such as when the reservoir is used as a suction canister, and/or vent ports.

The reservoir illustrated in FIGS. 2C and 2D may also optionally include a filter 270 in fluid communication with at least one of the fluid inlet ports 240. The filter 270 may provide for filtering debris from the fluid flowing through the reservoir, such as is illustrated and described in more detail below with reference to FIG. 5. Moreover, according to one embodiment, the filter 270 may be constructed from a non-rigid material to allow the collapsible reservoir 205, including the filter 270, to collapse, as illustrated in FIG. 2D, for example. A non-rigid filter 270 may optionally include a removable rigid or substantially rigid support frame, providing rigidity to the filter 270 and allowing it to withstand negative pressures.

Figure 3A:
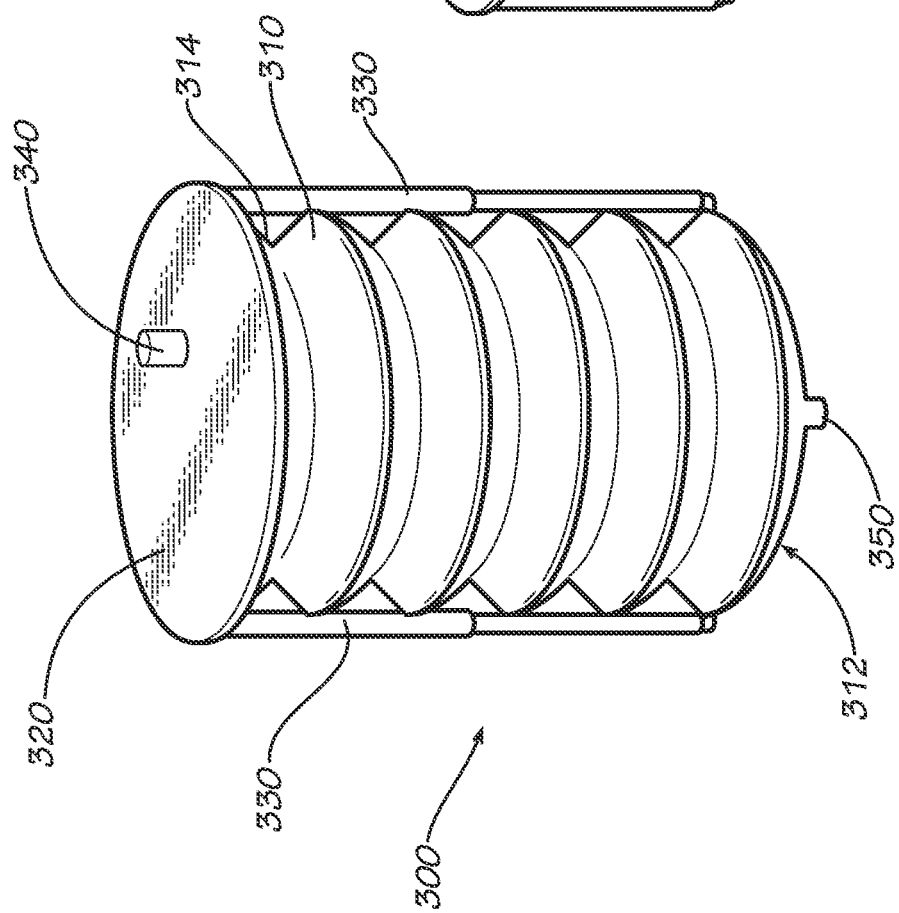
FIG. 3A illustrates an example collapsible reservoir in expanded configuration, according to one embodiment of the invention.
Figure 3B:
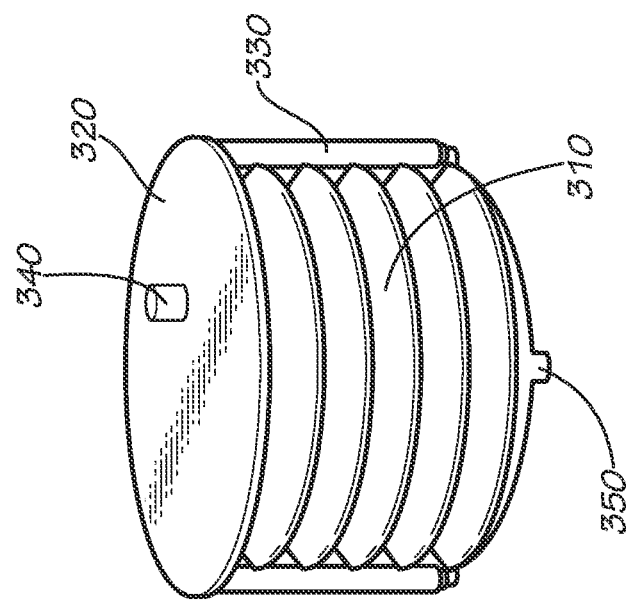
FIG. 3B illustrates an example collapsible reservoir in collapsed configuration, according to one embodiment of the invention.

FIGS. 3A and 3B illustrate another example embodiment of a collapsible reservoir. FIG. 3A illustrates an example collapsible reservoir 300 in expanded configuration, which includes a non-rigid container 310 formed with accordion-shaped walls, and including one or more expanding members 330 and a rigid cap 320 attachable to the proximal end of the non-rigid container 310. The non-rigid container 310 includes a substantially sealed distal end 312 and a substantially open proximal end 314, defining a volume in which blood or other fluids may be contained. The distal end 312 may optionally include at least one or more fluid outlet ports 350, which may be similar to that described above with reference to any of FIGS. 1A-1E. The rigid cap 320 may also be similar to that described above with reference to any of FIGS. 1A-1E.

The non-rigid container 310 of this embodiment has accordion-shaped walls to aid in collapsing and expanding the non-rigid container 310. For example, when not in use, the accordion-shaped walls of the non-rigid container 310 fold onto each other to lie in a substantially flat or reduced profile configuration. The non-rigid container 310 may be constructed in much the same manner as described above with reference to any of FIGS. 1A-1E. For example, multiple polyvinylchloride sheets may be sealed together to form the accordion shape. In another example, the rigid container is constructed from a semi-rigid polymer molded in the accordion shape. The non-rigid container 310 may attach to the rigid cap 320 in manners similar to those described with reference to any of FIGS. 1A-1E.

As illustrated in FIG. 3A, in one embodiment, the non-rigid container 310 further includes one or more expanding members 330. The expanding members 330 may be constructed of any rigid or substantially rigid material, such as from rigid polymers, metal, or the like. The expanding members 330 may attach to one or more points on the non-rigid container 310 and optionally to the rigid cap 320. In one embodiment, the non-rigid container 310 may include one or more loops or clips formed on its exterior surface for inserting the one or more expanding members and holding the non-rigid container 310 and the expanding members 330 in place. The expanding members 330 serve to hold the non-rigid container 310 in an expanded configuration. For example, the expanding members 330 may be formed from two members of different sizes such that one may be inserted and slide within the other. However, other configurations for the expanding members 330 that provide an ability to adjust the length of the member may be used. The expanding members 330 may further include a mechanism to lock the expanding member 330 at a desired length, such as a tension screw, a spring-actuated pin cooperating with one or more recesses, or the like. The expanding members 330 may be removably or permanently attached to the non-rigid container 310 and/or the rigid cap 320. In other embodiments, the expanding members 330 may not have an adjustable length; though, multiple expanding members 330 of differing lengths may be provided to allow selecting the length appropriate for the reservoir's intended use. It is further appreciated that in other embodiments, the collapsible reservoir 300 may not include any expanding members 330, and that the weight of the fluid contained within the non-rigid container 310 will cause the non-rigid container 310 to expand to sufficient size. Moreover, the accordion shape of the non-rigid container 310 provides lateral and radial rigidity to the non-rigid container 310 for withstanding inward radial collapse, such as may otherwise result if subjected to a negative pressure.

In one example embodiment, the collapsible reservoir 300 may further include a bottom support member (not illustrated) providing support to the distal end 312 of the non-rigid container 310 and optionally for connecting the distal ends of the one or more expanding members 330. The bottom support member may be configured as a frame constructed from one or more members, a basket, a substantially solid piece through which the fluid outlet port 350 may extend, or the like.

As illustrated in FIG. 3B, the collapsible reservoir 300 may be collapsed by the expanding members 330 to define a smaller volume for use during certain procedures. The collapsible reservoir 300 may also be stored in the collapsed configuration illustrated in FIG. 3B, reducing the size each reservoir occupies during storage. The expanding members 330 may optionally be removed during storage to allow for further compression of the accordion-shaped, non-rigid container 310. In example embodiments, the reservoirs may be distributed in sealed plastic in collapsed form such that the non-rigid container 310 lies substantially flat with the rigid cap 320 and the optional expanding members 330.

FIGS. 4A and 4B illustrate another example embodiment of a collapsible reservoir 400, which includes a non-rigid container 410, a coil-shaped supporting member 430 attached to the non-rigid container 410, and a rigid cap 420 attachable to the proximal end of the non-rigid container 410. The non-rigid container 410 includes a substantially sealed distal end 412 and a substantially open proximal end 414, defining a volume in which blood or other fluids may be contained, similar to that described above with reference to any of FIGS. 1A-1E. The distal end 412 may optionally include at least one or more fluid outlet ports 450, which may be similar to that described above with reference to any of FIGS. 1A-1E. The rigid cap 420 may also be similar to that described above with reference to any of FIGS. 1A-1E, for example, including at least one fluid inlet port 440.

In the embodiment illustrated in FIG. 4A, the coil-shaped supporting member 430 consists of a coil having a changing diameter. For example, the diameter may increase between its proximal end near the proximal end 414 of the non-rigid container 410 to its middle section at some point between the proximal end 414 and the distal end 412 of the non-rigid container 410, and decrease between its middle section and its distal end near the distal end 412 of the non-rigid container 410, creating a substantially elliptical or spherical shape. The coil-shaped member 430 of this embodiment serves to cause the non-rigid container 410 to expand and define a volume within the container. Moreover, the increasing and decreasing diameter of the coil-shaped member 430 allows it to collapse and lie substantially flat because each coil turn fits within (or around) the next coil turn, as is illustrated in FIG. 4B. The coil-shaped member 430 may be permanently or removably attached to the non-rigid container 410 in manners similar to those described above with reference to FIGS. 2A and 3A. In other embodiments, however, the coil-shaped member 430 may have a substantially constant diameter creating a cylindrical shape. In one embodiment, the coil-shaped member 430 is attached to the exterior surface of the non-rigid container 410, so as to not interfere with the fluid to be contained therein. In yet other embodiments, the coil-shaped member 430 may be attached to the interior surface or may be sandwiched between two sheets of the non-rigid container 410 or otherwise integrated therein.

In yet another embodiment, instead of a coil-shaped member, multiple concentric circular- or ring-shaped members having different diameters (e.g., increasing and decreasing), or substantially similar diameters (to create a cylinder shape) can be provided. This embodiment can achieve a similar effect to that illustrated in and described with reference to FIGS. 4A and 4B, allowing for expansion and collapse of the non-rigid container 410, while also providing structural strength and rigidity thereto.

The collapsible reservoir 400 illustrated in FIGS. 4A and 4B may be distributed in sealed plastic in collapsed form such that the non-rigid container 410 is integrated with the coil-shaped supporting member 430, allowing the container to lie substantially flat with the rigid cap 420, similar to that described with reference to FIGS. 1 and 2.

Any of the above-described example collapsible reservoirs may further include a filter, such as the filter 270 illustrated in FIGS. 2C and 2D, for filtering debris from collected fluid, and/or a defoamer or bubble trap for collecting gas bubbles in the fluid. For example, when used as a cardiotomy reservoir, a filter may be included with the collapsible reservoir to filter debris from the blood collected from the surgical site.

The filter may be integrated within the non-rigid container. For example, a filter may be included at or near the fluid inlet port or the fluid outlet ports or it may be positioned across the distal end of the non-rigid container upstream of the fluid outlet port. In one example embodiment, the rigid cap may include one or more fittings for attaching a filter to the underneath side of the cap prior to use, allowing fluid to flow through the one or more fluid inlet ports and through the filter prior to collection in the non-rigid container. In another example, a defoamer or bubble trap may be constructed from one or more layers of foam, such as one constructed from porous or microporous material, positioned within the non-rigid container in a manner similar to that described with reference to the optional filter. The defoamer or bubble trap can act to collect foam or other gaseous buildup, that may result from the turbulent pathway of the fluid, avoiding the introduction of foam downstream which may otherwise result in excess gas bubbles.

FIG. 5 illustrates one example embodiment of a filter 500 that may be used with a collapsible reservoir. The filter 500 may have a filter sleeve 505 constructed from a porous non-rigid material, such that it may be collapsed with the reservoir. When the reservoir is intended to be subjected to a negative pressure, for instance, when used as a cardiotomy reservoir, the filter 500 may further include one or more rigid filter frames 510, similar to those described with reference to FIGS. 2-4, to enable it to withstand such negative pressures. According to one embodiment, as illustrated in FIG. 5, the filter frame 510 may be removably positioned within the filter sleeve 505, such that the filter material may be stretched or otherwise positioned around the filter frame 510. In this embodiment, the filter frame 510 may be removed prior to packaging, shipping, storing, or disposal. In another embodiment, the filter sleeve 505 may be removably attachable within the filter frame 510, in a manner similar to that illustrated and described in FIGS. 2A-2D. In example embodiments, the filter frame 510 may be collapsible, for instance, in a manner similar to the reservoir support frames illustrated and described with reference to FIGS. 2A-2D, also allowing for collapse when packaging, storing, shipping, or disposing thereof. The filter frame 510 may be made from any rigid or substantially rigid materials described herein or otherwise suitable for such purposes. The filter 500 may be configured to be removably attachable to the underneath side of the rigid cap, such as is illustrated and described with reference to FIGS. 2C and 2D.

Each of the example collapsible reservoirs described above with reference to FIGS. 1-4 may include a means for attaching the reservoir to a pole, to a wall, for securing the reservoir on a flat surface, or the like. For example, a screw tension clamp may be included on the rigid caps, support frames, or the expanding members described above. In another example, a separate frame or basket that is attachable to a pole, wall, or a flat surface may be provided for holding the collapsible reservoir.

Accordingly, the embodiments illustrated and described herein provide example embodiments of collapsible reservoirs for use during medical procedures. These example reservoirs may be stored in a substantially flat or reduced profile configuration prior to use, reducing shipping costs, storage space, disposal volume, and disposal costs. Prior to use, the reservoirs can be expanded to a defined, and optionally adjustable, volume for containing and/or transporting fluid therein. Moreover, the reconfigurable nature of these example reservoirs, such as the ability to provide additional support frames, varied rigid cap configurations to include multiple inlet ports, venting ports, suction ports, or adjustable reservoir volumes, allow a single reservoir to be used in many applications. Example embodiments of the collapsible reservoirs described herein may be used as a cardiotomy reservoir, a venous reservoir, an arterial reservoir, or any other reservoir used for containing fluid and/or other matter before, during, or after medical procedures.

Many modifications and other embodiments of the inventions set forth herein will come to mind to one skilled in the art to which these inventions pertain having the benefit of the teachings presented in the foregoing descriptions and the associated attachments. Therefore, it is to be understood that the inventions are not to be limited to the specific embodiments disclosed and that modifications and other embodiments are intended to be included within the scope of the present disclosure. Although specific terms are employed herein, they are used in a generic and descriptive sense only and not for purposes of limitation. The scope of the invention is therefore intended to be limited solely by the scope of the appended claims.

What is claimed is:

1. A collapsible fluid reservoir comprising:
   a substantially non-rigid container comprising a substantially open proximal end and a substantially sealed distal end opposite the proximal end and defining a cavity therein, wherein the distal end comprises at least one fluid outlet port extending therethrough;

a substantially rigid support frame comprising a substantially open proximal end and a substantially open distal end, wherein the substantially non-rigid container is received within the substantially rigid support frame; and a substantially rigid cap affixed to the proximal end of the substantially non-rigid container or the proximal end of the substantially rigid support frame and comprising at least one fluid inlet port extending therethrough and in fluid communication with the cavity, wherein the substantially rigid support frame comprises a plurality of support members pivotally connected to one another at hinges.

2. The collapsible fluid reservoir of claim 1, wherein the collapsible fluid reservoir is one of: (i) a cardiotomy reservoir, (ii) a venous reservoir, or (iii) an arterial reservoir.

3. The collapsible fluid reservoir of claim 1, wherein the substantially rigid cap further comprises at least one vacuum port extending therethrough, in fluid communication with the cavity, and connectable to a vacuum source.

4. The collapsible fluid reservoir of claim 3, wherein the substantially rigid cap further comprises at least one of a valve or a filter in fluid communication with the at least one vacuum port.

5. The collapsible fluid reservoir of claim 1, wherein the substantially rigid cap further comprises at least one fluid outlet port.

6. The collapsible fluid reservoir of claim 1, wherein the substantially rigid cap further comprises a vent port extending therethrough and in fluid communication with the cavity.

7. The collapsible fluid reservoir of claim 1, wherein the substantially rigid cap is removably affixed to the proximal end of the substantially non-rigid container or the proximal end of the substantially rigid support frame.

8. The collapsible fluid reservoir of claim 1, further comprising a filter in fluid communication with at least one orifice in the substantially rigid cap.

9. The collapsible fluid reservoir of claim 8, wherein the filter is constructed from substantially non-rigid material.

10. The collapsible fluid reservoir of claim 8, wherein the filter further comprises a substantially rigid filter frame positioned within the filter.

11. The collapsible fluid reservoir of claim 9, wherein the filter is collapsible.

12. The collapsible fluid reservoir of claim 1, wherein the substantially rigid cap comprises: a circular geometry, an elliptical geometry, or an elongated rigid cap.

13. The collapsible fluid reservoir of claim 1, wherein the substantially rigid support frame is collapsible, and wherein the substantially non-rigid container is connected to the substantially rigid support frame at a plurality of connection points.

14. The collapsible fluid reservoir of claim 13, wherein the substantially non-rigid container is removably connected to the substantially rigid support frame at the plurality of connection points.

15. The collapsible fluid reservoir of claim 13, wherein when the substantially rigid support frame is in a substantially expanded configuration, the substantially non-rigid container is able to withstand a negative pressure of up to approximately −300 mmHg.

16. The collapsible fluid reservoir of claim 1, wherein the substantially non-rigid container comprises accordion-shaped walls.

17. The collapsible fluid reservoir of claim 1, further comprising a coil-shaped supporting member affixed to the substantially non-rigid container at a plurality of points between the proximal end and the distal end of the substantially non-rigid container.

18. The collapsible fluid reservoir of claim 1, wherein the substantially rigid cap is adapted for suspending the collapsible fluid reservoir from a pole when in use.

19. The collapsible fluid reservoir of claim 1, wherein the substantially rigid support frame is configured to pivot from a substantially expanded configuration to a substantially flat configuration.

20. The collapsible fluid reservoir of claim 1, wherein the substantially rigid support frame further comprises a locking mechanism configured maintain the substantially rigid support frame in the substantially expanded configuration.

21. The collapsible fluid reservoir of claim 13, wherein the substantially rigid support frame comprises a plurality of support members connected to one another in a telescoping manner.

22. The collapsible fluid reservoir of claim 21, wherein the substantially rigid support frame is configured to telescope from a substantially expanded configuration to a substantially compact configuration.

23. A fluid container, comprising:

a substantially non-rigid container comprising a substantially open proximal end and a substantially sealed distal end opposite the proximal end and defining a cavity therein, wherein the distal end comprises at least one fluid outlet port extending therethrough, and wherein the open proximal end defines a cross-sectional shape adapted for affixing to a rigid cap; and a substantially rigid support frame comprising a substantially open proximal end and a substantially open distal end, wherein the substantially non-rigid container is received within the substantially rigid support frame, wherein the substantially rigid support frame comprises a plurality of support members pivotally connected to one another at hinges.

24. The fluid container of claim 23, wherein the cross-sectional shape of the substantially open proximal end of the substantially non-rigid container is one of: circular, ovular, or polygonal.

25. The fluid container of claim 23, wherein the fluid container is one of: (i) a cardiotomy reservoir, (ii) a venous reservoir, or (iii) an arterial reservoir.

* * * * *